United States Patent [19]

Bell

[11] 4,258,441
[45] Mar. 31, 1981

[54] DUAL OPERATED LATERAL THUMB HAND PROSTHESIS

[75] Inventor: Judith A. Bell, New Orleans, La.

[73] Assignee: Hand Rehabilitation Foundation, Philadelphia, Pa.

[21] Appl. No.: 67,731

[22] Filed: Aug. 20, 1979

[51] Int. Cl.³ .............................................. A61F 1/06
[52] U.S. Cl. ...................................... 3/12.6; 3/12.1; 3/12.7
[58] Field of Search .................... 3/12.6, 12.7, 12.1, 3/12, 12.2, 12.3

[56] References Cited

U.S. PATENT DOCUMENTS

| | | | |
|---|---|---|---|
| 645,740 | 3/1900 | Schenk | 3/12.6 |
| 861,982 | 7/1907 | Hinz | 3/12.6 |
| 999,484 | 8/1911 | Carnes | 3/12.6 X |
| 1,046,966 | 12/1912 | Carnes | 3/12.7 X |
| 1,173,219 | 2/1916 | Rouley | 3/12.4 X |
| 1,206,753 | 11/1916 | Desmore | 3/12.6 X |
| 1,263,675 | 4/1918 | Jeffery | 3/12.8 |
| 1,277,747 | 9/1918 | O'Connor | 3/12.6 |
| 1,285,326 | 9/1918 | Nelson | 3/12.1 |
| 1,507,683 | 9/1924 | Pecorella et al. | 3/12.6 X |
| 1,989,960 | 2/1935 | Wheeler et al. | 3/12.1 |
| 2,409,884 | 10/1946 | Mollenhour | 3/12.7 |
| 2,493,041 | 1/1950 | Threewit | 3/12.6 X |
| 2,542,316 | 2/1951 | Farrar | 3/12.6 X |
| 2,668,959 | 2/1954 | Sargeson | 3/12.6 |

*Primary Examiner*—Barry Richman
*Attorney, Agent, or Firm*—Thomas A. Lennox

[57] ABSTRACT

A hand and lower arm prosthesis is provided for amputees who have the amputation stump of the lower arm muscularly connected to the upper arm, the prosthesis including a lateral thumb pinch utilizing a key grip with spring closure force connected to the upper arm elbow and in combination connected to the opposite shoulder to translate force of humeral flexion electively, alternately or in combination, with pronation and supination to the thumb pinch.

14 Claims, 6 Drawing Figures

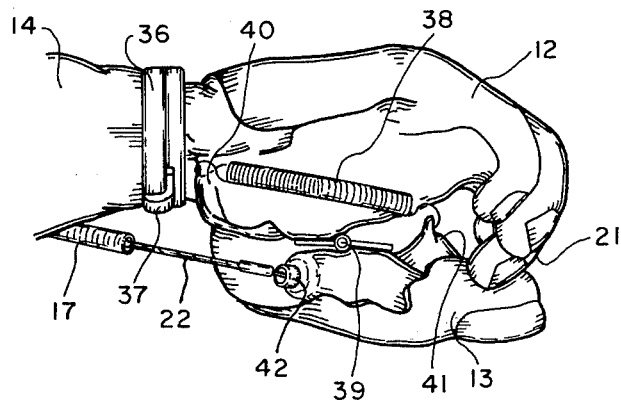
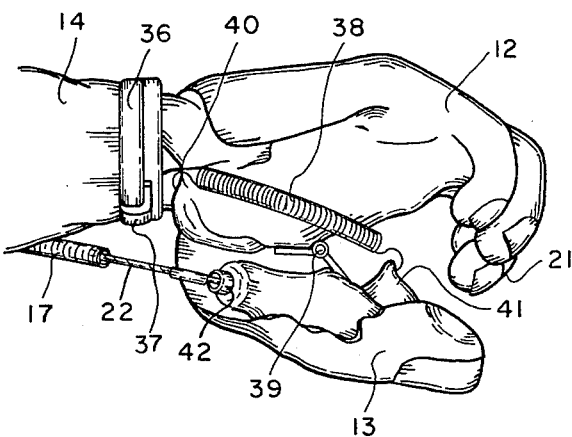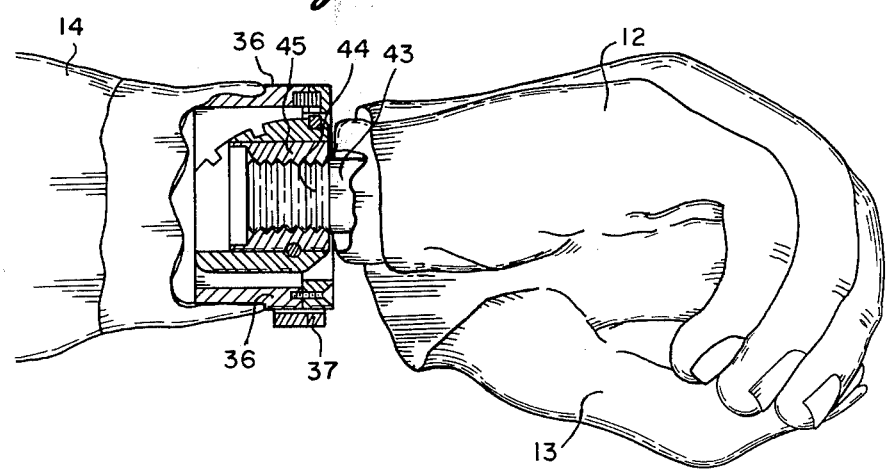

DUAL OPERATED LATERAL THUMB HAND PROSTHESIS

BACKGROUND OF THE INVENTION

This invention relates to hand prosthesis. Most of the hands produced for amputees are the old three jaw clinch construction. These hands provide tip prehension. The construction was intended to provide pinch and a crude grasp while the good hand would provide most necessary movement and more delicate handling. However, this device did not provide a secure grip or manipulative function for the amputee. These prior devices do not utilize movement that can easily be translated into a positional sense which is important to the amputee, as he redevelops his skills.

Essentially all of the activity in hand prosthesis has been directed to the tip pinch system which, as explained hereinabove, has been completely inadequate to satisfy the needs of the amputee. For example, in U.S. Pat. No. 1,173,219 to J. F. Rowley, an artificial hand is powered by connection to the same shoulder of the amputated hand and there is no purchase or connection to the upper arm and the strap to the other shoulder provides mere support.

U.S. Pat. No. 1,507,683 to A. Pecorella, et al., discloses an artificial hand with a fixed hinge connection at the elbow. There is and can be no connection between the lower arm amputation stump and the upper arm but only from the hand to the artificial forearm and then to the opposite shoulder.

A similar device is disclosed in U.S. Pat. No. 2,409,884, to B. C. Mollenhour which discloses an artificial arm and hand with cable connection from the hand to the forearm and then to the opposite shoulder with no connection or purchase from the posterior elbow. Additional patents which disclose various types of hand and arm prosthesis include U.S. Pat. No. 645,740 to H. Schenk, U.S. Pat. No. 1,206,753 to P. Desmore, U.S. Pat. No. 1,989,960 to F. E. Wheeler, et al., U.S. Pat. No. 2,542,316 to W. G. Farrar, Jr., U.S. Pat. No. 2,668,959 to J. Sargeson, U.S. Pat. No. 1,263,675 to B. Jeffrey, U.S. Pat. No. 1,285,326 to S. A. Nelson, U.S. Pat. No. 1,277,747 to E. L. O'Connor, and U.S. Pat. No. 861,982 to J. Hinz, Jr. None of these patents disclose or suggest the present invention and in particular do not utilize pronation or supination to power the grip. These hand prosthesis all fail to satisfy the following objects of this invention.

It is an object of this invention to provide amputees with below elbow disarticulation amputations, particularly those with wrist disarticulation amputations, with a functional cosmetic hand which allows the owner to control the position, motion, speed and pressure applied to operate a prosthetic thumb.

It is a further object of this invention to provide a key grip prosthetic hand with a lateral thumb pinch for which motive force and control is provided entirely by the amputee unless operational assistance is needed from external power.

It is an additional object of this invention to provide for opening of the prosthetic thumb in the usually more difficult planes of movement such as over the head, behind the back and close to the body.

It is an additional object of this invention to use purchase sensibility which may be translated through the prosthetic wearer to a positional sense of the prosthetic thumb.

It is a further object of this invention to provide a pinch prosthesis which is in an optimum line of vision of the person utilizing the prosthesis, making the prosthetic hand functional even in the absence of sensibility or in the presence of limited sensibility.

It is an object of this invention to provide a prosthesis with a simplified mechanism but yet facilitates translation of a position sense of a prosthetic thumb.

It is an object of this invention to provide a more effective grip which affords a firmer, more stable and easier grip of tools and objects thus freeing the uninjured hand as a manipulator during activities requiring bilateral function.

It is an object of this invention to provide an easy opening lateral thumb by the use of combined natural movements of the body.

It is an object of this invention to provide a functional use prosthesis in combination with a cosmetic hand that, by its movements and use, becomes even more cosmetic in providing the functions of a normal assistive hand.

It is finally an object of this invention to provide a prosthesis hand that allows the activities of daily living problems of the amputee, such as tying a shoe lace, a great deal easier.

SUMMARY OF THE INVENTION

A hand and lower arm prosthesis is provided for an amputee wherein the amputee's lower arm amputation stump remains muscularly connected to the upper arm. The prosthesis includes an amputation stump socket fitted over the stump, a hand prosthesis movably attached to the lower arm socket, a lateral thumb pinch mechanism in the hand prosthesis utilizing a key grip with spring means to provide closure force on the thumb pinch. A connection means is provided from the thumb pinch means to the posterior elbow to translate force of forearm pronation and supination as well as purchase sensibility to the lateral thumb pinch means. A continuing connection means from the posterior elbow to the opposite shoulder together with strap means to transfer force of humeral flexion of that shoulder to the thumb pinch means is preferred.

It is preferred that the movable attachment of the hand to the lower arm socket be by a flexion means to adjust the wrist angle together with a locking means to fix the wrist angle at the wearer's chosen position. It is also preferred that the wrist connection swivel to provide disarticulation of the hand.

BRIEF DESCRIPTION OF DRAWINGS

FIG. 4 is a perspective view of the lateral thumb pinch hand of the prosthesis of this invention showing the thumb in a closed position.

FIG. 5 shows the same hand illustrated in FIG. 4 with the thumb in the open position.

FIG. 6 is a perspective view with a partial cutaway cross-sectional view of the attachment system between the hand and the lower arm socket system.

DESCRIPTION OF PREFERRED EMBODIMENTS

Figure 1:
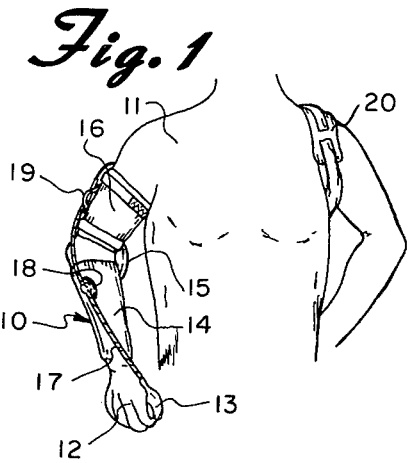
FIG. 1 is a partial perspective view of the torso and arms of a person wearing the prosthesis device of this invention.

In FIG. 1 hand prosthesis 10 is shown worn by amputee 11. Hand 12 with key grip thumb 13 is attached to stump socket 14 held in position by strap 15 and connected to cuff 16 around the posterior elbow. Cable 22 connects to thumb 13 on one end and includes casing 17 which is anchored to rigid connection 18 located on socket 14. Casing 17 slides through sliding connection 19 on cuff 16 and cable 22 is connected to opposite shoulder harness 20.

Figure 2:
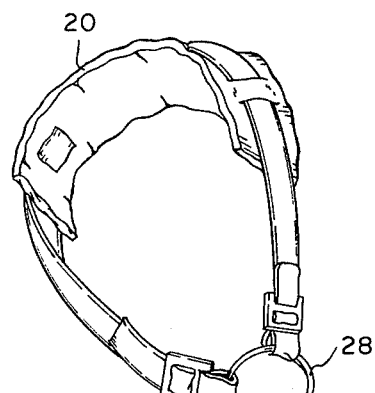
FIG. 2 is an expanded perspective view of the entire prosthesis device of this invention.
Figure 2:
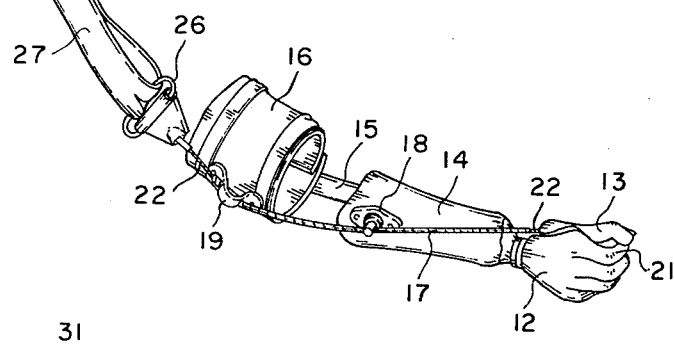

An expanded view of hand prosthesis 10, off of the wearer, is illustrated in FIG. 2. Hand 12 is fabricated of two thermoplastic molding materials offered commercially under trademarks KAY SPLINT from Fred Sammons, Inc., of Pennsylvania, and AQUAPLAST with finger patterns and hand shape individually molded in the shape of a cast of the amputee's normal hand. Thumb 13 is held against flat side 21 of stationary fingers by a spring mechanism illustrated in later figures. Cable 22 includes casing 17 which surrounds the internal cable. Cable 22 is 1/16 inch, Catalog No. C-100 from Hosmer Dorrance Corporation, 561 Division Street, Campbell, Calif. Cable 22 is rigidly attached to the base of thumb 13. Only a slight slack is provided in cable 22 and casing 17 is rigidly attached by rigid connector 18 to socket 14. The slight slack in cable 22 allows that when amputee's 11 stump is pronated, thumb 13 is pulled open. Cable 22 continues from connector 18 and is slidably attached through connector 19 to cuff 16, allowing casing 17 to slide through connector 19 but apply cutaneous pressure to the upper arm. Rotational pressure from excursion of cable 22 and casing 17 on the posterior humerous provides light touch to deep pressure sensibility on the posterior elbow. This pressure sense is utilized in a training program to teach positional sense to the thumb. Cable 22 is rigidly attached at 24 to hook 25 through which ring 26 is held to provide for a loop of strap 27 to be adjustably attached to ring 28 on which conventional shoulder harness 20 is attached. Thus by humeral flexion harness 20 transmits a pulling force through strap 27 on cable 22 thus providing sole force or a combination and additional force to open thumb 13.

Figure 3:
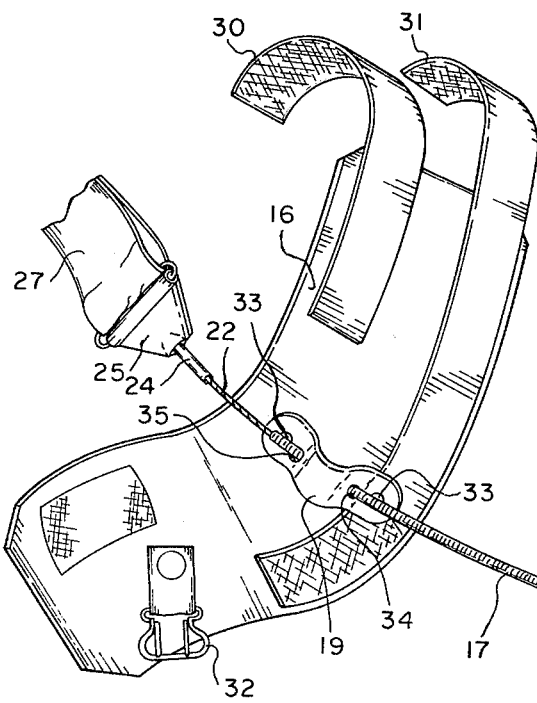
FIG. 3 is a perspective view of the attachment to the posterior elbow along with part of the cable system of the prosthesis device.
Figure 3:
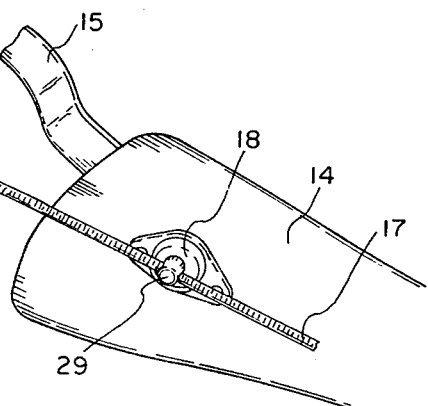

An expanded view of FIG. 3 shows a closer view of rigid connector 18 firmly gripping casing 17 at head 29. Cable 22 slides freely inside casing 17 at head 29. Cuff 16 is held in position by VELCRO straps 30 and 31 along with buckle 32 into which strap 15 is connected.

Slidable connector 19 is constructed by attaching U-shaped metal connector through rivets 33 and providing holes 34 and 35 through which cable casing 17 passes and may slide back and forth.

It should be understood that rigid connector 18 is shown here attached to the posterior lateral aspect of the forearm such that it will provide a guide for cable 22. By the tightness of the cable as it passes around the posterior elbow through connection 19 pronation or supination of the forearm results in motive force and control of the thumb. An equally useful alternative is to attach cable casing 17 through an identical attachment 18 at the anterior lateral aspect of the forearm. In that position, voluntary opening will be achieved upon forearm supination by amputee 11.

In FIG. 4 a close-up of hand 12 is shown as connected to stump socket 14 through flexible wrist unit 36, which allows hand 12 to be located in the straight position as shown or by depressing control button 37 to allow flexion to a 30 degree or 50 degree angle. Thumb 13 pivots on hinge 39 and is held in position against finger side 21 by a spring 38 connected between palm 40 and inside thumb connector 41. Cable 22 is connected to outside connnector 42 such that when cable 22 is pulled, thumb 13 will pivot on hinge 39 against resistance spring 38, Catalog No. 3-1976, from Hosmer-Dorrance above, to an open position as illustrated in FIG. 5. A removable KAY SPLINT plastic palm shield (not shown) covers the internal mechanism.

A partial cutaway cross-section of wrist unit 36 is shown in FIG. 6 imbedded in stump socket 14 cast of the KAY SPLINT. The entire flexion wrist unit 36 is available commercially from the Hosmer above as Catalog No. FL749. Hand 12 is attached to wrist unit 36 by imbedding wrist extender 43 also available commercially from Hosmer, Catalog Number FF-749. Wrist extender 43 was secured with AQUAPLAST molding compound available from W.F.R. Corporation 68 Birch Street, Ramsey, N.J. Threaded portion 44, engages threads 45 of wrist unit 36 to hold hand 12 securely into stump socket 14.

The preferred mechanism by which the prosthetic thumb is made to open voluntarily by the combination of motive forces by the wearer is to provide a combination cable connection from the thumb to the posterior elbow and to the opposite shoulder. An alternate means of accomplishing this result is to provide a rigid cable connection of the outside cover of the cable between the thumb and socket 14, but at the same time allowing the cable inside the casing to slide free inside rigid connection 18. Cable casing 17 and, of course, internal cable 22 is allowed to slide freely through sliding connection 19. It is at this point that pressure sense is developed by pressure of the cable to teach a positional sense of the thumb. Internal cable 23 is ultimately connected through the various straps to the shoulder harness on the wearer's opposite shoulder to provide additional motive force to the thumb, directly along the cable.

The combination or alternation of control and force through supination and pronation, plus or through humeral flexion provides a unique and quite controllable movement by the wearer. This dual action or election of operation provides coordinated movement by the prosthetic wearer and facilitates easier opening of the prosthetic thumb. The one thumb lever is operated against the fixed portion of the prosthetic finger base by both forces in combination. Translation of the position sense from the elbow cutaneous receptor is to the single lever. While not necessary, it is sometimes useful to provide a plate or air bladder under cuff 16 directly under connection 19 to provide cutaneous reception distributed over a larger area of the elbow.

Hand prosthesis 10 harnesses the motive force of humeral flexion which, coordinated with pronation and supination opening, provides for more coordinated movements of the prosthetic wearer. The humeral flexion force applied at 19 on cable 22 may override the pronator or supinator force in situations where the selective positioning of the hand is necessary and rotation is not desired, i.e. holding a cup of coffee.

The prosthesis 10 may be easily modified to provide either a voluntary opening on forearm supination or in the alternative, provide voluntary opening on forearm pronation. Similarly, prosthesis 10 may be adjusted to voluntarily open on humeral flexion or in the alternative, voluntarily close on humeral flexion. Thus, humeral flexion force may be used selectively, alternately or in combination with pronation and supination muscles and function force, all directed to the thumb pinch. A positional sense of the prosthetic thumb is translated from a cutaneous receptor at connector 19.

While prosthesis 10 utilizes one cable 22 which, together with casing 17 held secure at 29 and the tightness of cable 22 from ring 28 to connector 42, provides the multiplicity and combination of control of the force, multiple cables may be used. For example, a cable can run from connector 42 to head 29 or, in the alternative, the posterior elbow, and terminate at that point. An alternative provides a cable running from connector 42 to head 29, sliding freely or firmly attached at that point, and then continuing to a connection on cuff 16 at the posterior elbow, terminating at that point. A second cable, in combination with any of the above shorter cable systems, can run from connector 42, slide freely through head 29, slide through sliding connector 19 and firmly attach to end attachment 24. A cutaneous receptor would be placed under cuff 16 or could be provided inside socket 14.

While I have described my invention in connection with specific embodiments, it is to be clearly understood that this description is made only by way of example and not of limitation to the scope of my invention as set forth in the following claims.

I claim:

1. A hand and lower arm prosthesis for amputees whose amputation stump of the lower arm remains muscularly connected to the upper arm, comprising:
   (a) an amputation stump socket and brace means fitting over the amputation stump;
   (b) a prosthetic hand movably attached to the amputation stump socket;
   (c) a lateral thumb pinch means providing a key grip between the thumb and the hand;
   (d) a spring means to provide a continuous closure force on the thumb pinch means holding it against the hand; and
   (e) a posterior elbow connection means connecting the thumb, the socket, and the posterior elbow of the amputated arm, said connection means translating force of forearm pronation and/or supination to open the lateral thumb pinch means and of providing purchase sensibility to the posterior elbow.

2. The hand prosthesis of claim 1 wherein the movable attachment between the hand and the stump socket is a pivot connection to allow the wrist to be angled in a plane and a locking means to secure the pivot at a chosen angle.

3. The hand prosthesis of claim 1 wherein the attachment between the hand to the stump socket is a swivel means connection to provide disarticulation of the hand.

4. The prosthesis of claim 1 wherein the elbow connection means connects the posterior elbow to the shoulder opposite the amputation whereby stabilization of the shoulder transfers force of humeral flexion of the arm with the prosthesis or pronation and supination of the prosthetic forearm, or both, to the thumb pinch means.

5. The hand prosthesis of claim 4 wherein the posterior elbow connection means comprises a cuff under which an air pillow is inserted as a cutaneous receptor means.

6. The hand prosthesis of claim 4 wherein the posterior elbow connection means is connected to the posterior lateral aspect of the forearm and includes a cutaneous receptor means against the elbow.

7. The hand prosthesis of claim 4 wherein the posterior elbow connection means is connected to the anterior lateral aspect of the forearm and includes a cutaneous receptor means against the elbow.

8. The hand prosthesis of claim 1 wherein the posterior elbow connection means is a cable attached to the base of the thumb pinch means at a position such that tension on the cable will pull the thumb away from the hand against the spring pressure.

9. The hand prosthesis of claim 8 wherein the cable is encased and only the case is rigidly attached to the stump socket, the cable case being slidably connected to an upper arm strap which provides cutaneous pressure on the posterior elbow and the cable being rigidly connected to a strap which is in turn rigidly connected to a second strap surrounding the shoulder opposite the disarticulated arm and connected with minimal slack, to transfer humeral flexion to the thumb pinch means.

10. The hand prosthesis of claim 9 wherein the posterior elbow connection means is a cable attached to the base of the thumb pinch means at a position such that tension on the cable will pull the thumb away from the hand against the spring pressure.

11. The hand prosthesis of claim 10 wherein the shoulder connection means is a cable attached to the base of the thumb pinch means at a position such that tension on the cable will pull the thumb away from the hand against the spring pressure.

12. A hand and lower arm prosthesis for amputees whose amputation stump of the lower arm remains muscularly connected to the upper arm, comprising:
   (a) an amputation stump socket and brace means fitting over the amputation stump;
   (b) a prosthetic hand movably attached to the amputation stump socket;
   (c) a lateral thumb pinch means providing a key grip between the thumb and the hand;
   (d) a spring means to provide a continuous closure force on the thumb pinch means holding it against the hand;
   (e) a cuff around the upper arm just above the elbow;
   (f) a posterior elbow connection means connecting the thumb, the socket and the cuff at the posterior elbow, said connection means translating force of forearm pronation and/or supination to open the lateral thumb pinch means and of providing purchase sensibility to the posterior elbow.
   (g) a shoulder connection means connecting the cuff at the posterior elbow to the shoulder opposite the amputation whereby stabilization of the opposite shoulder transfers force of humeral flexion of the arm to open the thumb pinch means; and
   (h) a cutaneous receptor means providing cutaneous pressure from the connection means to amputee.

13. The hand prosthesis of claim 12 wherein the posterior elbow connection means and the shoulder connection means is a cable attached to the base of the thumb pinch means at a position such that tension on the cable will pull the thumb away from the hand against the spring pressure.

14. The hand prosthesis of claim 13 wherein the cable is encased and only the case is rigidly attached to the stump socket, the cable being slidably connected to the cuff which provides cutaneous pressure on the posterior elbow and the cable being rigidly connected to a strap which is in turn rigidly connected to a second strap surrounding the shoulder opposite the disarticulated arm and connected with minimal slack to transfer humeral flexion to the thumb pinch means.

* * * * *